United States Patent [19]

Molina-Negro et al.

[11] Patent Number: 4,541,432
[45] Date of Patent: Sep. 17, 1985

[54] ELECTRIC NERVE STIMULATOR DEVICE

[75] Inventors: Pedro Molina-Negro, Montreal; Roger Garceau, Pierrefonds, both of Canada

[73] Assignee: Neurotronic Ltee, Montreal, Canada

[21] Appl. No.: 450,722

[22] Filed: Dec. 17, 1982

[51] Int. Cl.$^4$ .............................................. A61N 1/36
[52] U.S. Cl. ............................................... 128/421
[58] Field of Search .......... 128/419 E, 419 F, 419 C, 128/420–423

[56] References Cited

U.S. PATENT DOCUMENTS

| | | | |
|---|---|---|---|
| 3,478,744 | 11/1969 | Leiter | 128/423 R |
| 3,727,616 | 4/1973 | Lenzkes | 128/422 |
| 3,800,800 | 4/1974 | Garbe et al. | 128/423 |
| 3,888,261 | 6/1975 | Maurer | 128/421 |
| 3,897,789 | 8/1975 | Blanchard | 128/422 |
| 3,911,930 | 10/1975 | Hagfors et al. | 128/422 |
| 3,983,881 | 10/1976 | Wickam | 128/421 |
| 4,121,594 | 10/1978 | Miller et al. | 128/422 |
| 4,153,059 | 5/1979 | Fravel et al. | 128/422 |
| 4,240,437 | 12/1980 | Church | 128/420 R |
| 4,256,116 | 3/1981 | Meretsky | 128/421 |
| 4,324,253 | 4/1982 | Greene et al. | 128/421 |
| 4,431,000 | 2/1984 | Butter et al. | 128/421 |

FOREIGN PATENT DOCUMENTS 2504395 10/1982 France .............................. 128/421

Primary Examiner—William E. Kamm
Assistant Examiner—Mitchell Shein
Attorney, Agent, or Firm—Oblon, Fisher, Spivak, McClelland & Maier

[57] ABSTRACT

An electric nerve stimulation device and apparatus for suppressing organic pain and other functional disorders of the nervous system without noxious sensation and substantially free from the adaptation phenomenon which usually results from subjecting receptors and nerve cells to uniform stimulating signals. The device includes a pulse generator to produce bipolar rectangular waveforms at preselected repetition rate and of a preselected width during a given first time period. Electronic circuits are connected to the post generator to deliver rectangular waveforms at a repetition rate which is chosen by a pseudo-random function for a second time period which is also chosen by a pseudo-random function. Further circuitry is provided to inhibit delivery of pulse waves for a third period of time. This third period of time is chosen by a pseudo-random function, thereby substantially eliminating noxious sensations and adaptation of nerve cells to stimulation during suppression of the organic pain. Electrodes are connected to the output of the device to apply the waveforms to nerve fibers to be stimulated thereby.

12 Claims, 8 Drawing Figures $T_2 = \alpha T_1$ $A_2 = A_1/\alpha$ $A_1 \cdot T_1 = A_2 \cdot T_2$

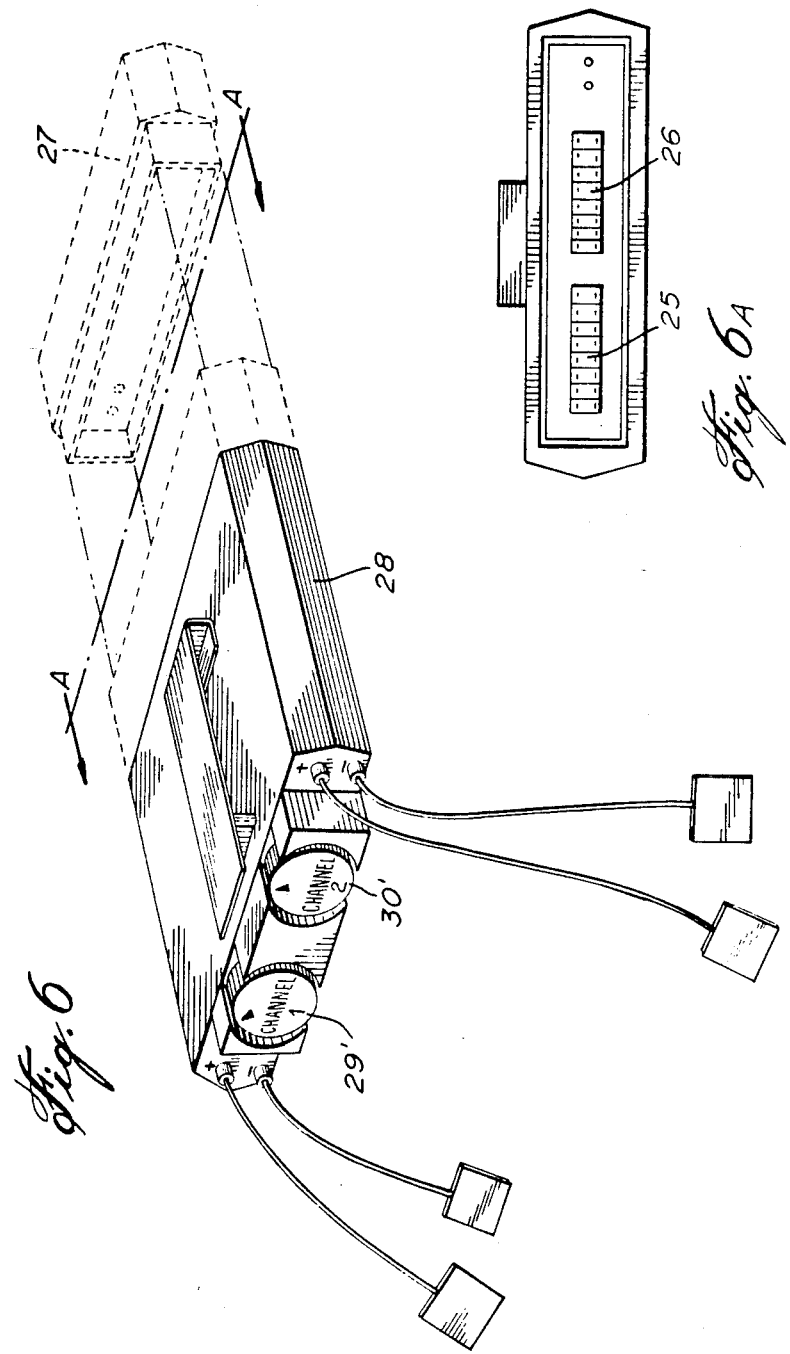

4,541,432

ELECTRIC NERVE STIMULATOR DEVICE

BACKGROUND OF THE INVENTION (a) Field of the Invention

The present invention relates to an electric nerve stimulation and more particularly to a transcutaneous nerve stimulating device and method for suppression of organic pain and other functional disorders of the nervous system, without noxious sensation and substantially free from the nerve cell adaptation phenomenon.

(b) Description of Prior Art

Electrotherapy of pain and motor disorders was made possible with the development of modern electronics. The most important single factor that opens a new era in electrotherapy was the publication by Melzack and Wall in 1965 of their work on gate theory of pain from which it is evidently shown that in order to suppress pain it was necessary and sufficient to electrically stimulate the thicker strong myelinated fibers which are responsible for the transmission of touch, vibration and pressure. According to the authors of the gate theory such stimulation would result in inhibition of the transmission of impulses in the thinner unmyelinated fibers carrying noxious information.

In the majority of prior art devices, transcutaneous stimulators were proposed to suppress organic pain by generating pulse through the skin to stimulate the peripheral nerve fibers, whereas the noxious sensations were eliminated by varying the pulse amplitude, pulse duration and/or pulse repetition rate, thereby placing very restrictive parameters on the operation of such devices. However, this treatment did not eliminate the adaptation phenomenon of receptors and nerve cells to sensor impulses. In this respect, U.S. Pat. No. 3,817,254 to Maurer proposes to introduce a variation in the pulse repetition rate to overcome the adaptation phenomenon by providing a ram generator as an input to a pulse generator.

SUMMARY OF THE INVENTION

The invention provides an improved transcutaneous nerve stimulating device and method that produces a pulse signal capable of suppressing organic pain over long periods of time without noxious sensations by the patient while avoiding the nerve fibers to adapt to the treatment signal.

It is therefore a feature of the present invention to provide a nerve transcutaneous device effective in suppressing organic pain by generating biphasic and bipolar pulse waves and without transmission of noxious sensations.

It is a further feature of the present invention to provide a nerve transcutaneous stimulator that inhibits adaptation of nerve fibers to the stimulating pulse waves.

It is a still further feature of the present invention to provide a method of suppressing organic pain by transcutaneously injecting a series of rectangular pulse waves into nerve fibers in a sequence such as to prevent transmission of noxious sensations and to avoid adaptation of the fibers to the stimulating waves.

According to a broad aspect of the present invention there is provided an electric nerve stimulating device which suppresses organic pain in a body. A pulse generating means is provided for supplying a series of bipolar rectangular waves. The generating means includes means to preselect the width and the repetition rate of the waves over a predetermined period of time. A further generating means is connected to the bipolar rectangular wave generating means for delivering a series of rectangular waves having a repetition rate and width which is chosen by a pseudo-random function over a period of time different from the bipolar rectangular wave generating period, and which is chosen by a pseudo-random function. Thereafter, means are provided to inhibit delivery of any wave over a third period of time. Means is also provided to apply the waveforms to nerve fibers to be stimulated thereby.

The invention also relates to a method of stimulating nerve cells including the step of generating into the fibers a series of bipolar rectangular pulses having a preselected width and repetition rate during a first period of time followed by the generation of rectangular pulses at a repetition rate chosen by a pseudo-random function for a second period of time while inhibiting delivery of any wave during a third time period. The pulses are applied to nerve fibers to be stimulated thereby.

BRIEF DESCRIPTION OF THE DRAWINGS

A preferred embodiment of the present invention will be hereinafter described with reference to the examples illustrated by the accompanying drawings, in which:

FIG. 6 is an isometric view of the portable apparatus resulting from the second examples of the invention, and FIG. 6a is a cross-section view along cross-section lines A—A of FIG. 6.

DESCRIPTION OF PREFERRED EMBODIMENTS

As mentioned previously, studies have demonstrated that transcutaneous electric stimulation of the thicker strong myelinated fibers responsible of the transmission of touch, vibration pressure was an effective method of suppressing pain. Such a stimulation inhibits the low velocity conduction fibers which are thinner than the myelinated fibers and responsible for the transmissive of noxious sensations. For that purpose, a waveform having a fast rise and fall time and being bipolar is provided in order to prevent adverse electric and thermal effects by maintaining the wave positive charge equal to the negative charge through the delivery of a signal having a total nil value. Furthermore, whereas the problem of transmission of noxious sensation was sufficiently well handled by previous nerve stimulators, another problem was less accurately solved and concerns the quick adaptability of the nerve fibers to external stimulations. This results in a decrease of the efficiency of the stimulating device. The stimulation device and method advocated herein achieves a substantial relief of such adaptation phenomenon.

Figure 1:
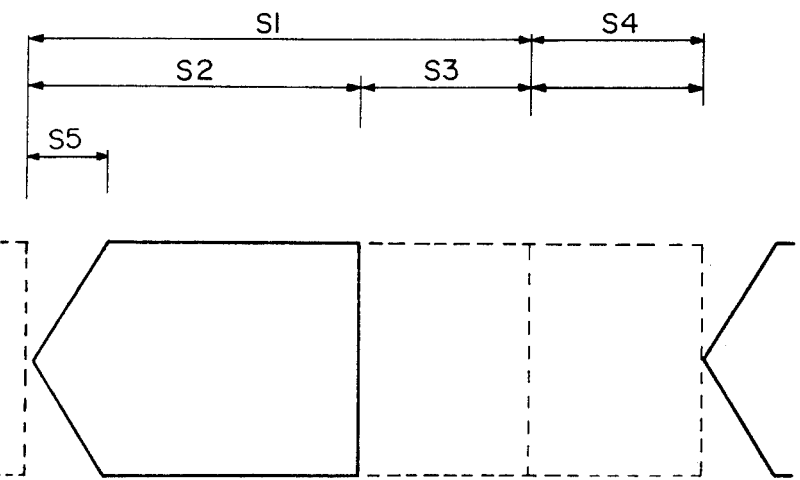
FIG. 1 is a diagram illustrating the treatment method for stimulating nerve cells in accordance with the present invention.

Referring to FIG. 1, there is illustrated the repetitive sequence of stimulating pulses which are transcutaneously injected into the nerve fibers. Each sequence has a time duration ranging from 32 to 40 seconds, wherein the nerve fibers are submitted to bipolar rectangular pulse waves for an overall time period S1. During that period S1, the nerve cells are first stimulated through the injection of a series of steady bipolar rectangular pulses having a preselected pulse duration or width as well as a preselected repetition rate. Period S2 is usually set at about 30 seconds and is immediately followed by a second period of stimulation S3, while the duration varies from 1 to 5 seconds. The frequency of the pulses varies from 35 to 65 cps. Both the duration and the frequency of pulses are selected in a random mode. Period S4 corresponds to a time "off" during which no waves are being injected into the nerve cells and the latter period is also made variable according to a random function and may range from 1 to 5 seconds. Therefore, by varying at random periods S3 and S4 from one sequence to another efficient stimulation of the nerve fibers is achieved without production of any noxious sensation and moreover without the adaptation phenomenon. This anti-adaption mechanism may be furthermore enhanced by providing a ramp function at the very start of each sequence to gradually increase the amplitude of the rectangular pulses during a time period S5 to about 5 seconds, as shown in the instant example.

In cases where the chosen frequency of the main period is inferior to 20 cps, this will be immediately followed by the S4 period and then S3 period will be eliminated.

Figure 2A:
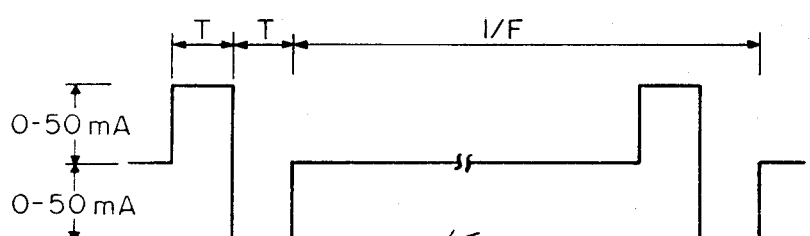
FIGS. 2a and 2b show types of pulse waves provided for stimulating the nerve cells.
Figure 2:
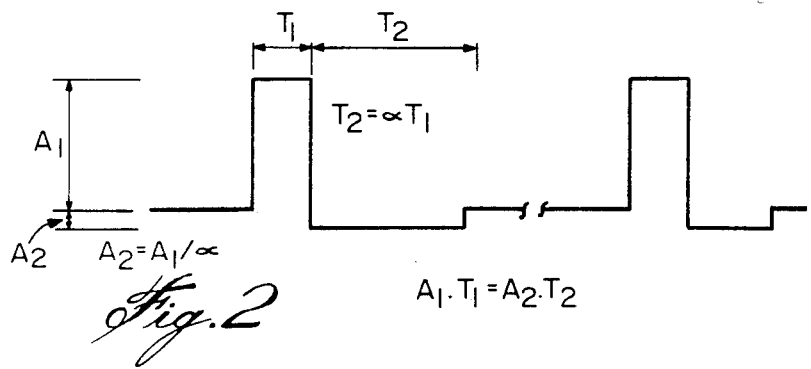

Referring to FIGS. 2a and 2b, there is shown rectangular pulse waves effective in achieving the required stimulation effects of the nerve cells. The two pulses are both bipolar and are of a constant amplitude. In FIG. 2a, the pulse is shown symmetrical in that the positive half weight is similar to the negative counterpart with identical pulse duration or width. The amplitude itself may vary from 0 to 50 mA when an impedance ranging from 100 to 500 ohms per channel is used whereas the pulse duration may vary from 50 to 250 micro-seconds with an effective repetition rate and frequency ranging from 1 to 100 hertz. An important factor and characteristic of the pulse wave is that the charge per phase is lower than 0.45 mC per pulse and that the current intensity is lower than 175 mC per square centimeter per half pulse, in order to avoid any tissue damage in prolonged use of transcutaneous stimulation and even more for implanted devices.

The pulse wave illustrated in FIG. 2b is provided with most of the characteristics of that of FIG. 2a except that the negative part of the wave has an amplitude much lower and a width much longer than the previous one. However, the energy distribution between the positive and negative parts has been maintained equal since the relation A1 to T1 equals that of E2 to T2. It is to be noted that whether the pulse wave of FIG. 2a or 2b is used, the amplitude always remains constant during the main period of effective stimulation of the nerve cells.

Figure 3:
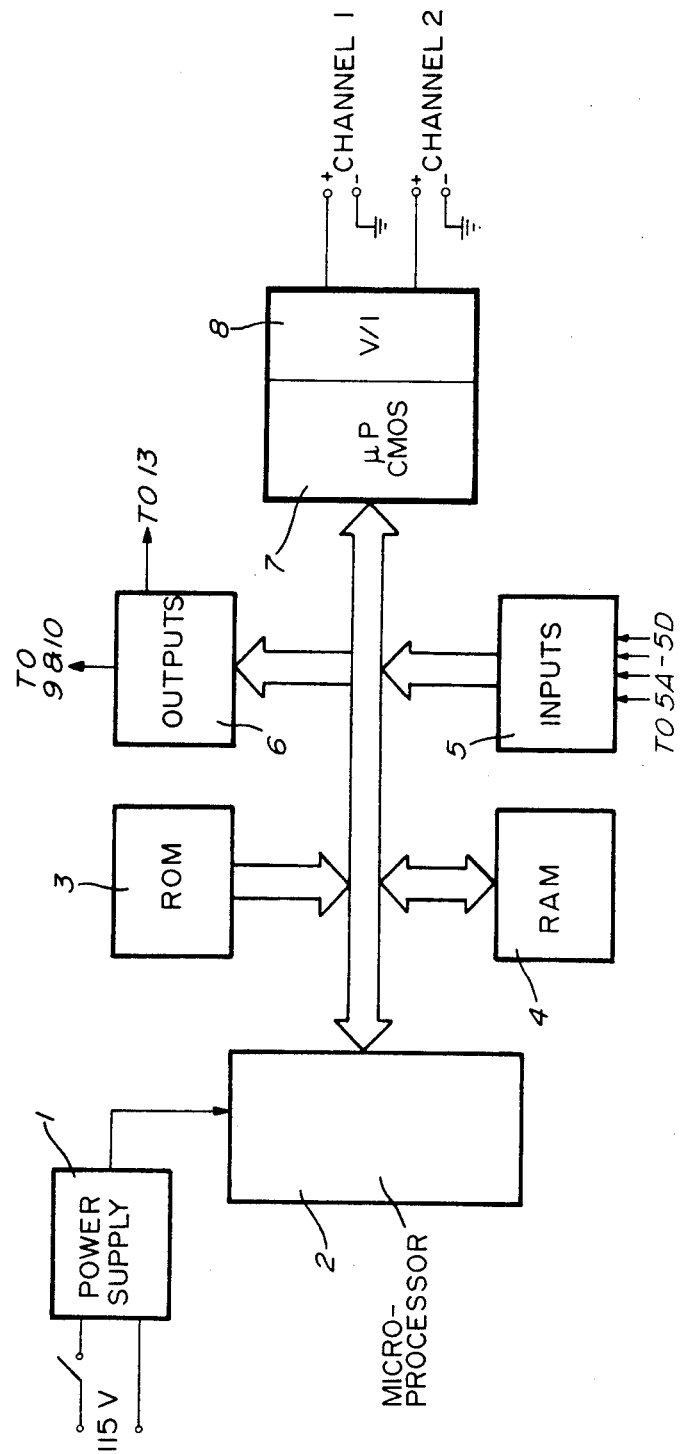
FIG. 3 is a block diagram of a first example of the transcutaneous stimulating device of the present invention.
Figure 4:
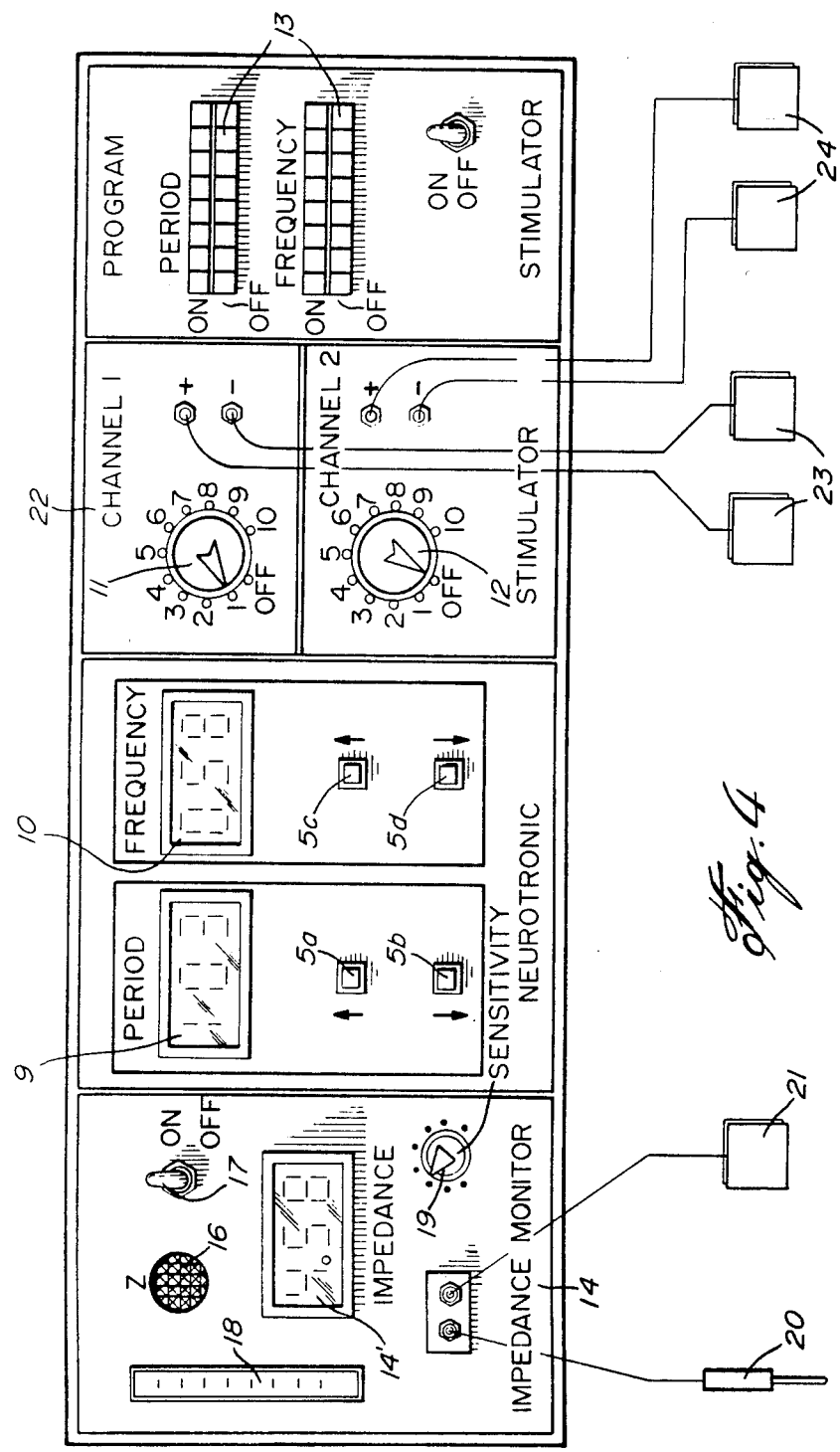
FIG. 4 is a front view of a laboratory apparatus resulting from the first example of the invention.

Turning now to FIGS. 3 and 4, there is illustrated, respectively, a block diagram of the parts constituting the nerve stimulating device and the physical representation thereof. The stimulating device shown in FIG. 4 is often intended to be suitable for use by a physician or by trained specialists commonly found at therapeutic clinics. The stimulating device includes a power supply 1 feeding a microprocessor 2 which generates the required bipolar rectangular pulses for time periods S2 and S3 indicated in FIG. 1 and is operatively connected to the read only memory (ROM) 3 as well as to the random access memory (RAM) 4 so as to allow determination of the optimum parameters in terms of pulse duration or width and repetition rate. The method for determining accurately those optimum parameters is however beyond the scope of the present invention since they vary from one patient to another and also in accordance with the type of pain to be suppressed and the type of functional disorders of the nervous system to be treated and therefore are specific to each case encountered.

It is noted that the two most important parameters to vary to achieve optimum treatment results are the pulse duration and frequency rate of the stimulating wave. With the device, those two parameters are made variable. The duration of the pulse may range from 50 to 250 micro-seconds by increments of 2.5 micro-seconds by pressing any one of the push button switches 5a and 5b whereas the repetition rate is changed from 1 to 100 hertz through increments of 1 hertz by actuating push button switches 5c or 5d. Then pressing either switches 5a or 5c will increase the corresponding parameter by a one unit value whereas pressing switches 5b or 5d, the parameter value will be decreased by one unit value. If one of the switches is pressed for a period of time greater than 2 seconds, then the corresponding parameter will be increased or decreased at a rate of 10 units per second. For ease of reference, the parameters are each digitally displayed at 9 and 10 on the face of the unit. Once determined, those operational parameters are used to program a further microprocessor 7 the values of which are displayed at 13 on the stimulating device. The output current generated by the microprocessor 7 is stabilized and made constant by means of a feedback circuit 8 connected to a double channel output, each of the latter being connected to a pair of electrodes 23 and 24, respectively. The function of the feedback circuit 8 is to ensure that the output current remains constant even if the skin impedance for any reason varies from time to time. Furthermore, the amplitude or intensity of the output current of each channel is made adjustable from 0 to 50 milliamps by means of the step knob switches 11 and 12, respectively.

The arrangement illustrated in FIG. 4 further comprises an impedance monitor 14 which serves to measure the patient's skin impedance and more particularly to locate the low impedance points of the body in the vicinity of the nerve cells to be stimulated. The circuitry of that impedance monitor 14 is not shown herein since it is of conventional design, known in the art. The monitor has two electrodes, a ground electrode 21 and a pencil-like electrode 20. The ground electrode 21 is held by the patient in his hand whereas the probe 20 is moved over the skin to locate the low impedance or high conductance points of the skin. Knob switch 19 is used to select various sensitivity skills of impedance. The monitor 14 emits a more or less continuous sound through a buzzer 16 as the skin impedance decreases. Conversely, the sound impulses will be at one interval as the impedance increases. A bar indicator 18 indicates the relative value of the measured impedance whereas a digital display 14 is used to locate accurately the highest conductance value whenever a low impedance zone is located. Switch 17 is the ON/OFF switch for the monitor. Monitor 14 may measure impedance values ranging from 0 to 5 meg ohms by using a low current sensor.

Figure 5:
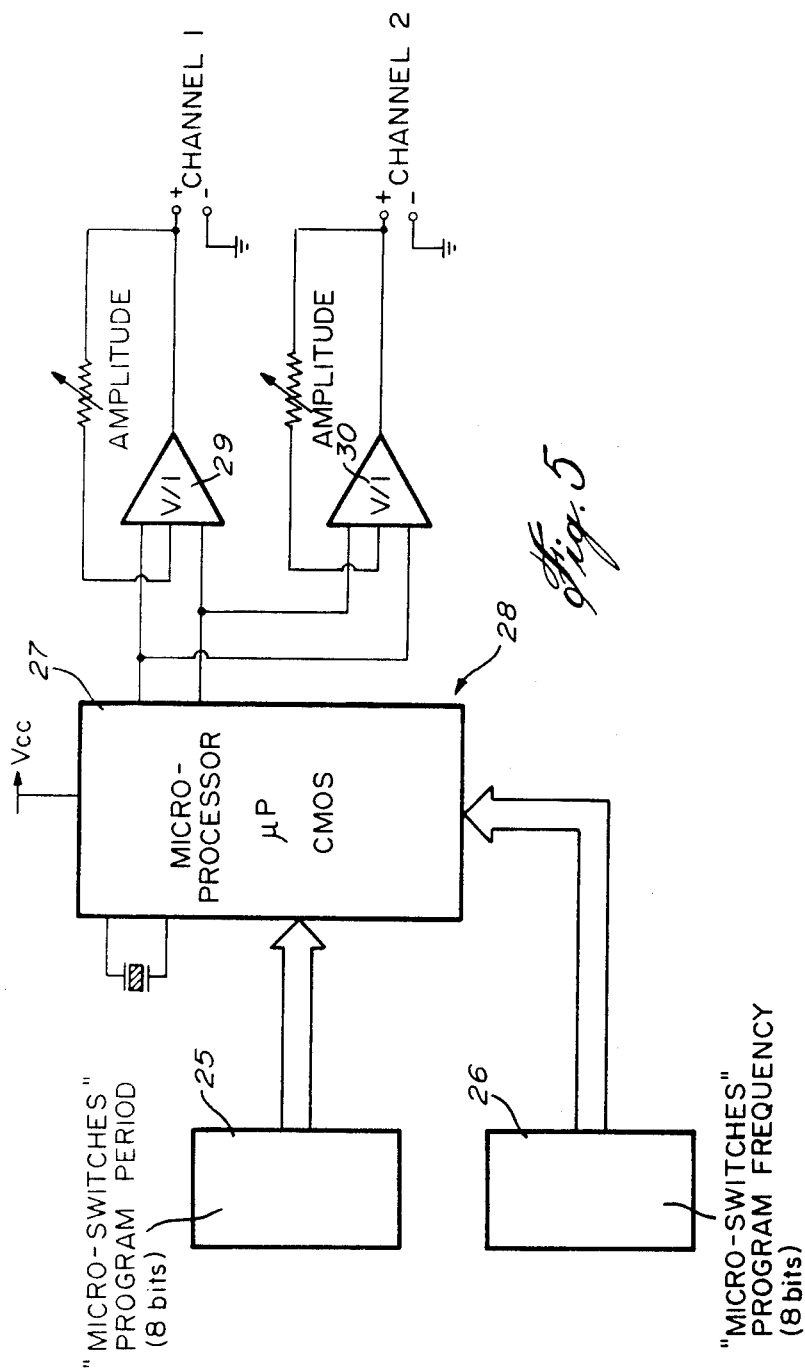
FIG. 5 is a block diagram of a further example of the invention and relative to a portable stimulating device.

Referring generally to FIGS. 5, 6 and 6*a*, there is shown a portable version of the nerve stimulating device intended to be used by a patient. As shown in the block diagram of FIG. 5, the portable stimulator 28 is generally made up of circuit components similar to circuits 7 and 8 of FIG. 3. In fact, to ensure that the portable stimulator will deliver pulse waves of the same nature than that of the stimulator shown in FIGS. 3 and 4, the same type of microprocessor 27 as well as of voltage to current converters 29 and 30, each having a feedback loop, are provided. However, in the case of the portable stimulator, the pulse duration as well as the repetition rate thereof cannot vary but remain constant. To achieve this, a set of micro-switches 25 is provided to preset the pulse duration whereas the micro-switches 26 preset the repetition rate value. Those micro-switches 25 and 26 are programmed in accordance with the values set on the programming circuit 13 of FIG. 4 as provided by the outputs 6 from FIG. 3. Knob switches 29' and 30' allow the user to vary the intensity of the output current from 0 to 50 milliamps for each channel. The stimulator of FIG. 6 is powered by a low voltage DC battery.

Summarizing, there are characteristics defining the function of the present invention. Some of them are partially shared by other devices known in the art. However, the ensemble of all five makes the present electrical neurostimulator an original instrument for the control of pain and many other functional disorders of the nervous system.

The use of a biphasic and bipolar pulse waveform of a positive square wave followed immediately of a symmetrical negative square wave provides a maximum of efficacity and suppresses all possibility of tissue damage due to electrolitic effect. Many of the so-called allergic reactions to the electrolitic gel or the electrodes are in fact the result of skin damage produced by the current itself. The use of a monopolar wave could be admitted in transcutaneous stimulations at least when it is well tolerated. On the contrary, the use of a constant current bipolar pulse wave is essential in implanted devices.

The fact that the threshold of stimulation is much lower for the discriminative touch and increases progressively for the vibration, pressure, pricking and temperature permits a selective stimulation of a particular group of fibers thus providing the basis for a directed modulation of the sensory message. One can theoretically suppress a neural pain, relax a spasmodized muscle or reinforce a semi-paralized muscle by acting specifically in a particular group of fibers. Such specificity of electrical stimuli can be obtained with the present neurostimulator by means of accurate, biofeed-back balanced pulses, with all three parameters (pulse width, frequency and current intensity) adjustable at will for each case in particular. Objective reading of such parameters permits on the other hand a record of the effects of stimulation for purpose of comparison from patient to patient and from one time to another in the same patient. Instead of the present empirism that prevent the comparison of results from one individual to another the possibility of objective criteria is available.

As a result of what has been said, the possibility and the necessity of a programmation for each particular problem and each individual, becomes evident. The present device provides this possibility of programmation of all parameters by the therapist leaving to the patient only the control of the intensity. On the other hand, the present model of neurostimulator permits the modification of the program simply by manipulation of controls.

Adaptation and habituation are well known phenomena of sensory receptors and of nerve cells. Fast adaptation to sensory impulses is characteristic of receptors and nerve cells connected by fast conducting fibers, deserving phasic phenomena. An example of these are discriminative and propioceptive sensations that provide fast and precise information essential for the refined mechanisms of voluntary movement. On the other hand, show adaptative receptors and nerve cells acting through slow conducting fibers are involved in tonic, long lasting phenomena, such as chronic pain. Due to the high degree of adaptability of such type of fibers, the efficacity of the stimulation decreases very fast. It is a common observation that the current is felt much weaker after a few seconds. The increase of intensity in such cases could result in an activation of slow conducting fibers, thus diminishing the duration and the degree of analgesia.

A much rational approach of the problem of adaptation is made with the present electrical neurostimulator in which each period of stimulation of 30 seconds is followed by a period of 1 to 5 seconds of duration with a certain frequency, these two parameters (duration and frequency) are chosen in a random mode. This first anti-adaptive period is followed by a pause of a random duration from 1 to 5 seconds followed in turn by the main period of stimulation according to the program selected.

The present knowledge permits a most rational choice of the points of application of the electrodes than the current empiric methods. The comparison of meridians and accupuncture points with the motor points leads to the conclusion that most of the latter coincides with one or another of the former. The evidence is growing concerning the possibility that the remaining accupuncture points correspond to the trigger points that can be more accurately called sensory points.

In order to obtain the maximal efficacity possible, the electrodes shall be placed either in close vicinity of a sensory or accupuncture point for the treatment of pain. On the contrary, if the condition under treatment is a motor disorder, the electrode should be placed at the motor points. A common characteristic of the sensory and motor points is their lower skin resistance. The present invention provides an impedance probe with visual and acoustic controls that permit easy location of the optimal point of stimulation.

It is within the ambit of the present invention to provide any obvious modification of the examples described herein provided such modifications fall within the scope of the appended claims.

We claim:
1. An electric nerve stimulating device for suppression of organic pain in a body, comprising:
   pulse generating means for producing bipolar rectangular waveforms at a preselected repetition rate and of a preselected width during a given first time period;
   means connected to said pulse generating means to deliver rectangular waveforms at a repetition rate and width which is chosen by a pseudo-random function and different from said preselected rate and width of said bipolar rectangular waveforms, for a second time period;

means connected to said pulse generating means for inhibiting delivery of pulse waves for a third time period different from said first and second time period, thereby substantially eliminating noxious sensations and adaptation of nerve cell to stimulation during suppression of the organic pain;

means connected to said pulse generating means to gradually increase the amplitude and width of said bipolar rectangular waveforms according to a start ramp mode;

feedback means connected to said pulse generating means to stabilize the amplitude of said bipolar and random rectangular waveforms; and means connected to said pulse generating means to apply said waveforms to nerve fibers to be stimulated thereby.

2. A stimulating device as claimed in claim 1, wherein said pulse generating means include means to vary said preselected pulse width from 50 $\mu$sec to 250 $\mu$sec.

3. A stimulating device as claimed in claim 2, wherein said pulse generating means include means to vary said preselected pulse repetition rate from about 1 to 100 hertz.

4. A stimulating device as claimed in claim 3, wherein said repetition rate varying means include means to change said rate by increments of 1 hertz.

5. A stimulating device as claimed in claim 2, wherein said varying means includes means to vary the pulse width by increments of 2.5 $\mu$sec.

6. A stimulating device as claimed in claim 1, wherein micro-switches are provided to preset the values of said preselected pulse width and repetition rate.

7. A method for stimulating nerve cells transcutaneously for suppression of organic pain, comprising the steps of:

generating a series of bipolar rectangular pulses having a preset duration and a preset repetition rate during a first time period, wherein at start of said first period, a ramp function is generated to vary gradually the amplitude and width of said bipolar pulses;

generating a series of random rectangular pulses at a time immediately following delivery of said bipolar pulses for a second time period;

inhibiting said generation of pulses for a randomly varying period of time; and applying said pulses to nerve fibers to be stimulated thereby.

8. A method as claimed in claim 7, wherein said preset duration ranges from 50 to 250 $\mu$sec.

9. A method as claimed in claim 7, wherein said preset repetition rate varies from 1 to 100 hertz.

10. A method as claimed in claim 7, wherein said random pulses has a freqence range varying from 35 to 60 hertz.

11. A method as claimed in claim 7, wherein said bipolar pulses are symmetrical waveforms.

12. A method as claimed in claim 7, wherein said bipolar pulses are quasi-monophasic with a positive amplitude value much higher than the negative value.

* * * * *